United States Patent [19]

Cobia

[11] Patent Number: Plant 6,042

[45] Date of Patent: Oct. 20, 1987

[54] CACTACEAE PLANT

[75] Inventor: Barnell L. Cobia, Winter Garden, Fla.

[73] Assignee: B. L. Cobia, Inc., Winter Garden, Fla.

[21] Appl. No.: 739,441

[22] Filed: May 30, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new sterile plant variety has many of the characteristics of the 'Lavender Doll' variety and in comparison to this variety has about the same growth rate, tendency to branch when pruned, and specimen size at maturity. It has a greater natural tendency to branch without pruning, a much greater tendency to form more compact specimens with a more upright and erect posture at maturity and the phylloclades are usually shorter in length and narrower in width. The new variety has a greater resistance to nutrient deficiencies and known problem diseases of the related varieties and it is more resistant to bud abscission and provided with a greater tendency to form multiple buds on the branch tips. It has a habit of producing more blooms with about the same bloom life as that of the 'Lavender Doll' variety but at a noticeably earlier date in the blooming season. The blooms of the new variety closely resembles the bloom of the 'Lavender Doll' variety in color but at full bloom appears more robust and may be distinguished therefrom by a shorter perianth tube, a sepaloid series of tepals that have a smaller number of tepals which have shorter length dimensions and narrower blade widths, a tube laminating series of tepals with shorter length dimensions and a tube forming series of tepals that have longer length dimensions and slightly greater blade widths.

4 Drawing Figures

The invention relates to a new and distinct plant variety of the Cactaceae family and which has been named the *Zygocactus truncatus* 'Lavender Doll II' by the inventor.

Certain plant varieties of the Cactaceae family are well known in the foliage plant market and among these are the varieties of the *truncatus* species of the Zygocactus genus and which are commonly referred to as "Christmas Cacti" for they tend to bloom in the months of November and December in the Northern Hemisphere and hence appear in the retail market area primarily during the Thanksgiving and Christmas seasons.

Among the various *Zygocactus truncatus* varieties is the 'Lavender Doll' variety. This variety is a fertile variety that has a generally "purplish" colored bloom and its characteristics are set forth in U.S. Plant Pat. No. 3,690.

A general objective of the invention has been to develop a variety of the Cactaceae family which provides a bloom that closely resembles the 'Lavender Doll' variety in color but which produces sterile specimens that exhibit a more compact (denser) growth habit and a more upright and erect posture at maturity than the 'Lavender Doll' variety. Yet another objective has been to develop a sterile variety of the *truncatus* species of the Zygocactus genus which provides blooms that closely resemble the 'Lavender Doll' variety in color and in bloom life, but which mature at an earlier date than those of the 'Lavender Doll' variety so that the demand for such bloom colors in the market place can be met earlier during the marketing season. Still another objective has been to develop a variety with a bloom similar to that of the 'Lavender Doll' variety but which is more robust in appearance and has a habit of forming more of such blooms on specimens of comparable size and maturity in comparison to the 'Lavender Doll' variety.

The objectives of the invention have been fully realized by the development of the new plant variety hereinafter described in detail. The new plant variety was developed in a nursery located at Winter Garden, Fla. from a seed pod secured by self pollination on a specimen of an unnamed research variety that is a descendant of the 'Kris Kringle' variety that is characterized by a "reddish" colored bloom and forms the subject matter of U.S. Plant Pat. No. 3,688. The seeds taken from the fertilized seed pod were cultivated at the mentioned nursery location and after prolonged observation of the seedlings, the plant of the new plant variety was selected and asexually reproduced by the inventor at the Winter Garden nursery by the propagation of stem cuttings taken from the original plant. The unnamed research variety has not appeared in the market area.

Through successive propagations, it has been ascertained that specimens of the new plant variety generally resemble the 'Lavender Doll' variety but are distinguishable from specimens of this variety and the parent variety and other related varieties known to the inventor, by a growth habit which is evident in plant specimens propagated and grown under nursery conditions utilized in the growing of tropical plants at Winter Garden, Fla., as combining the following principal characteristics:

1. A growth rate, tendency to branch when pruned and specimen size at comparable stages of maturity that are about the same as those of the 'Lavender Doll' variety.

2. A greater natural tendency to branch without pruning and a much greater tendency to form more compact specimens with a more upright and erect posture at maturity than the 'Lavender Doll' variety, the phylloclades on such specimens being usually shorter in lengths and narrower in widths than those of the 'Lavender Doll' variety.

3. More resistance to bud abscission and a slightly greater tendency to form multiple buds on the branch tips than exhibited by the 'Lavender Doll' variety.

4. A slightly greater resistance to nutrient deficiencies and known problem diseases of the related variety in comparison to the 'Lavender Doll' variety.

5. A habit of producing more blooms with about the same bloom life (6–8 days) and at a noticeably earlier date (7–10 days) in the blooming season on specimens of comparable maturity and size when compared with the 'Lavender Doll' variety.

6. A bloom which in color closely resembles the bloom of the 'Lavender Doll' variety, but which at full bloom appears more robust and may be distinguished therefrom by a. a sepaloid series of tepals that have a smaller number of tepals, and tepals with shorter length dimensions and narrower blade widths,
b. a tube laminating series of tepals that have tepals with shorter length dimensions,
c. a tube forming series of tepals that have tepals with longer length dimensions and slightly greater blade widths, and
d. a perianth tube which is conspicuously shorter in length.

7. Specimens that are sterile.

The accompanying drawings serve by color photography to illustrate the new plant variety and wherein one sheet photographically illustrates a 12 month old plant specimen that was propagated in March and pruned to two tiers above the propagated stem cutting in July of the year of propagation. Yet another sheet photographically illustrates a pair of phylloclades and attached blooms, one being seen in the process of opening and the second at full bloom. The third and fourth sheets photographically illustrate the bloom, with one sheet illustrating the bloom as generally seen along the axis of the perianth tube and the other illustrating the bloom more or less from the side and at an acute angle to the axis of the perianth tube.

The following is a detailed description of the new plant variety with colors and hues, unless otherwise clearly indicated by the text through the absence of color notations being named in accord with the ISCC-NBS Method of Designating Colors, (U.S. Dept. of Commerce, National Bureau of Standards, Circular 553, issued Nov. 1, 1955) the named colors being interpreted from color notations derived by comparison with the color specimens in the "Neighboring Hues Edition" of the Munsell Book of Color, published by the Munsell Color Company, Inc. of Baltimore, Md. The description is further based on observations of well fertilized plants of less than two years of age from initial propagation and which were grown under 50–75% shaded glasshouse nursery conditions in the Winter Garden, Fla. area and wherein temperatures range from about 60° F. to about 85° F. during the winter months, from about 75° F. to about 95° F. during the summer months, and are otherwise ambient during the intervening periods.

I. Name: *Zygocactus truncatus* 'Lavender Doll II'.

II. Parentage: A self pollinated product of ZH9636-T, an unnamed research variety which in comparison to the new plant variety is a less compact, slightly slower growing variety with less frequent branching and a less erect posture. The parent has a slightly larger bloom with slightly wider tepals which may be considered as generally "reddish" in color. Its perianth tube is also longer than the new variety.

III. Classification:

A. *Botanic* (*Britton and Rose, The Cactaceae,* Constable and Co., Ltd., London 1937, vol. IV).—(1) Family: Cactaceae. (2) Tribe: Cereeae. (3) Subtribe: Epiphyllanae. (4) Genus: Zygocactus. (5) Species: *truncatus* (Haworth) Schumann.

B. *Commercial.*—Thanksgiving-Christmas blooming cactus.

IV. Form: Epiphylic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extension of the vascular system to the marginal teeth. (b) Texture — Smooth, waxy epidermis with wax in small embedded scales and becoming woody in basal stem areas with specimen aging. (c) Size (at maturity) — 1. Length: Usually between 18 and 45 mm. 2. Thickness: Usually between 2 and 14 mm. (d) Color (at maturity) — Usually moderate olive green (7.5 GY 4/6) (7.5 GY 4/4) and/or moderate yellow green (5 GY 5/6) (7.5 GY 5/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1–2 mm. in the area intermediate the margin and midrib. 2. Width: Usually 8–18 mm. as measured from phylloclade axis to most offset lateral areole. 3. Color (at maturity): Usually strong yellow green (7.5 GY 6/8), moderate yellow green (7.5 GY 6/6) (7.5 GY 5/6) and/or moderate olive green (7.5 GY 4/6) (7.5 GY 4/4). (4) Teeth: (a) Shape — 1. General: Generally flattened and tapered along the margins and from the wing insertion to an apex having a hyaline, single cell, pointed spine with non-predictable bending of both the abaxial margins and adaxial margins. 2. Adaxial margin: Usually straight to convex. 3. Abaxial margin: Usually concave. (b) Orientation — Usually project distally of phylloclade and laterally of the phylloclade axis in an alternate arrangement with some tendency toward an opposite arrangement occasionally being evident. (c) Margins — Entire, with thin, clear marginal areas that are more pronounced in adaxial areas. (d) Texture — Succulent to leathery with smooth waxy epidermis having wax in smooth embedded scales of density comparable to wings, and becoming corky in basal stem areas with specimen aging. (e) Size (at maturity) — 1. Thickness: Usually 0.05–1.5 mm. in center area. 2. Areole to apex dimension (adaxial marginal side): Usually 8–10 mm. in the upper quadrants of the phylloclades. (f) Number — Usually 4–6 per phylloclade. (g) Color — Usually strong yellow green (7.5 GY 6/8), moderate yellow green (7.5 GY 6/6) (7.5 GY 5/6) and/or moderate olive green (7.5 GY 4/6) (7.5 GY 4/4). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth at the distal end of the phylloclade. (b) Axillary areoles — Acicular bristles without glochidia but having copious, short, brownish, wooly hairs. In areoles located below the teeth at the distal end of the phylloclade, there is usually only one areole which is frequently latent.

VI. Buds: Unarmored, ovoid and chlorphyllous.

VII. Flowers:

A. *General.*—Sessile, zygomorphic, usually solitary, terminal, perfect and epigynous with double hypanthium and whorled tepals (undifferentiated sepals and petals) and having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–5. (5) Size (at full bloom): (a) Length (base-tip dimension) — Usually less than 15 mm. (b) Width (maximum) — Usually less than 12 mm. (6) Color (at full bloom): Varies from the outer members to the inner members with the smallest outer tepals usually having a continuous field that in color is dominated by a yellow green hue. The inner whorl tepal members having marginal blades areas that in color are dominated by a purplish pink hue that merges inwardly along the axis of the blade with a white area constituting a distal projection of a translucent white color in the basal area. Commonly light purplish pink (5 RP 8/6), moderate purplish pink (5 RP 7/8) and/or pale purplish pink (5 TP 9/2) in the marginal areas of the inner whorl members and light yellow green (5 GY 8/4) (5 GY 8/6), strong yellow green (5 GY 7/8) and/or moderate yellow green (5 GY 7/6) in the basal areas of outer whorl members. (7) Orientation: Erect to recurve at full bloom.

C. *Tube laminating series.*—(1) General: Tepals inserted on ovary and basally united below the throat as outer laminations on the perianth tube and with progressively greater amounts of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 7–9 tepals. (5) Size (at full bloom): (a) Length (base-tip dimension) — Usually between 18 and 50 mm. (b) Width (maximum) — Usually between 12 and 20 mm. (6) Color (at full bloom): (a) General — Tepals with translucent white basal areas and marginal blade areas that in color are dominated by purplish pink and/or purplish red hues which usually merge with the distally extending basal are a color along the tube attached area. (b) Basal area — Translucent white at insertion and usually purplish white (5 RP 9/1), pinkish white (10 RP 9/1), pinkish gray (10 RP 8/1), pale yellow green (10 Y 9/2) and/or yellowish white (10 Y 9/1) along tube attached area. (c) Marginal blade area — Usually deep purplish pink (5 RP 6/10) and/or moderate purplish red (5 RP 5/10). (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and ellipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex area. (c) Carina (keel) — Degenerate and reduced to a slight superior extension of the perianth tube. (3) Texture: (a) Perianth tube — Thick, succulent and slightly ribbed. (b) Blades — Translucent and silken. (c) Carina (keel) — Fleshy. (4) Number: Usually 8–10. (5) Size (at full bloom): (a) Perianth tube — 1. Length (base-keel): Usually 22–28 mm. along tube axis. 2. Major axis: Usually 9–12 mm. at throat interior. 3. Minor axis: Usually 7–10 mm. at throat interior. (b) Blades — 1. Length (keel-tip): Usually 30–45 mm. 2. Width (maximum): Usually 16–20 mm. (6) Color (at full bloom): (a) Perianth tube — A basic field that is translucent white at the basal area of the field and usually purplish and/or pinkish in coloration distally of the basal area. Commonly purplish white (5 RP 9/1), pale purplish pink (5 RP 9/2) and/or pinkish white (5 R 9/1). (b) Blades — Marginal blade areas that in color are dominated by a purplish pink hue which merges with the distally extending coloration of the perianth tube. Commonly moderate purplish red (5 RP 5/10) and/or dark purplish pink (5 RP 6/8). (c)

Carina (keel) — Color dominated by deep pink and/or purplish red hues. Commonly moderate purplish red (10 RP 5/8) and/or deep pink (10 RP 6/10). (7) Orientation: Acute to recurve.

E. *Androecium* (*stamens*).—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 67–78. (b) Basally united group — Usually 19–25. (3) Filaments: (a) General — Translucent with anther connective. (b) Shape — Long, slender, terete. (c) Texture — Glabrous and capillaceous. (d) Color — Translucent white. (e) Size (at full bloom) — 1. Length: (a) Tube attached group — Usually between 41 and 45 mm. (b) Basally united group — Usually between 46 and 52 mm. 2. Diameter: Usually 0.2–0.5 mm. intermediate insertion and distal end. (4) Anthers: (a) General — Adnate with four longitudinally dehiscent pollen sacs and connective inserted at end. (b) Shape — Elongated. (c) Texture — Waxy. (d) Color (before dehiscence) — Commonly yellowish white (near 2.5 Y 9/2) and/or pale yellow (2.5 Y 9/4). (e) Sterility — Sterile.

F. *Gynoecium* (*pistil*).—(1) General: Exserted with compound, pariental placentation and united style surrounded by annular diffuse yellowish nectary at its insertion. (2) Style: (a) General — Stout and inserted at ovary. (b) Shape — Elongated and terete. (c) Texture — Fleshy and smooth. (d) Color — Dominated by purplish pink and/or purplish red hues. Commonly deep purplish pink (7.5 RP 6/10), moderate purplish red (5 RP 5/10) (7.5 RP 4/8) and/or moderate purplish pink (5 RP 7/8). (e) Size (at full bloom) — 1. Length: Usually 60 to 64 mm. 2. Diameter: Usually 0.7–1.0 mm. intermediate opposite ends. (3) Stigma: (a) General — Exserted and erect with usually 6–8 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Dominated by a purpish red hue. Commonly moderate purplish red (7.5 RP 5/8) (10 RP 5/8) (5 RP 5/10). (e) Lobe size — 1. Length: Usually 3–4 mm. along inner margins. (4) Ovary: (a) General — Inferior with thin epidermis and usually 6–7 carpules with numerous ovules. (b) Shape — Terete to ovoid and generally broadening from insertion to floral end. Ribbed single concavity with inserted style. (c) Texture — Succulent with glanrous thin outer epidermis. (d) Color — Usually strong yellow green (2.5 GY 6/8) and/or moderate yellow green (5 GY 5/6) (2.5 GY 5/6). (e) Size — 1. Length: Usually 10–12 mm. from insertion to cavity base. 2. Major axis: Usually 8–10 mm. at distal end of concavity.

VIII: Growth Habit: The new plant variety has about the same rate of growth, tendency for branching when pruned, and size at comparable stages of growth, as compared to the 'Lavender Doll' variety. However, it forms more compact (denser) specimens and exhibits more frequent branching without the need for pruning than the 'Lavender Doll' variety. It also has a more erect posture by comparison at maturity.

The new plant variety, as compared to the 'Lavender Doll' variety has a slightly greater resistance to nutrient deficiencies and a slightly greater resistance to known problem diseases of the related varieties such as Pythium and damp-off fungii.

The blooms produced by the new variety on specimens of comparable age as compared to those of the 'Lavender Doll' variety are more resistant to bud abscission. There is a greater tendency to form multiple buds on the branch tips and the blooms of the new variety have about the same bloom life (6–8 days) as those of the 'Lavender Doll' variety but they appear in the blooming season at a noticeably earlier date (7–10 days) than those of the 'Lavender Doll' variety.

The bloom of the new plant variety closely resembles the bloom of the 'Lavender Doll' variety in color. However, the bloom of the new variety has a more robust appearance and may be distinguished from that of the 'Lavender Doll' variety by a. a sepaloid series of tepals that have a smaller number of tepals, and tepals with shorter length dimensions and narrower blade widths,
b. a tube laminating series of tepals that have tepals with shorter length dimensions,
c. a tube forming series of tepals that have tepals with longer length dimensions and slightly greater blade widths, and
d. A perianth tube which is conspicuously shorter in length.

In addition to the above, specimens of the new plant variety are sterile.

The following is a general description of a specimen of the new plant variety which was grown from the propagation of a single phylloclade in a nursery at Winter Garden, Fla.

Age of plant: 20 months from initial propagation of single phylloclade and pruned twice, once in the 6th month to the second tier above the propagated phylloclade and again in the 17th month to the third tier above the propagated phylloclade.
Branches from propagated phylloclade: 2.
Total number of new phylloclades grown from propagated phylloclade: 56.
General:

| Branch No. | No. of Phylloclades | Max. Length | No. of Tips |
|---|---|---|---|
| 1 | 22 | 45 mm. | 7 |
| 2 | 34 | 43 mm. | 11 |

Midribs:

| Branch No. | Length (avg.) | Thickness (avg.) |
|---|---|---|
| 1 | 32.8 mm. | 4.27 mm. |
| 2 | 33.05 mm | 4.14 mm. |

Wings:

| Branch No. | Center Thickness (avg.) | Max. Width (avg.) |
|---|---|---|
| 1 | 1–2 mm. | 29.27 mm. |
| 2 | 1–2 mm. | 29.41 mm. |

Teeth:

| Branch No. | No. per Phylloclade (avg.) | Center Thickness (avg.) | Areole to Apex Length (avg.) |
|---|---|---|---|
| 1 | 5.05 | .7–1.3 mm. | 8.0 mm. |
| 2 | 5.35 | .7–1.3 mm. | 8.1 mm. |

Phylloclade color: Moderate yellow green (5 GY 5/6) and/or moderate olive green (7.5 GY 4/6) (7.5 GY 4/4).

The following is a general description of a flower of the new plant variety and which bloomed in December on the 20 month old plant specimen mentioned above and which was grown under shaded greenhouse nursery conditions in Winter Garden, Fla.

No. of buds and blooms on plant specimen: 27.
Bloom life: 8 days.
Sepaloid series of tepals:
*Number.*—4.
*Size (at full bloom).*—Maximum base-tip dimension: 14 mm. Minimum base-tip dimension: 6 mm. Maximum width dimension: 12 mm.
*Color (at full bloom).*—Light purplish pink (5 RP 8/6) and/or moderate purplish pink (5 RP 7/8) in continuous field of outer whorl members of small tepals. Pale purplish pink (5 RP 9/2) and/or purplish white (5 RP 9/1) in marginal and center field areas and light yellow green (5 GY 8/4) (5 GY 8/6) (5 GY 7/8) in the basal areas of the inner whorl members.
Tube laminating series of tepals:
*Number.*—9.
*Size (at full bloom).*—Maximum base-tip dimension: 50 mm. Minimum base-tip dimension: 18 mm. Maximum blade width: 20 mm. Minimum blade width; 12 mm.
*Color.*—Deep purplish pink (5 RP 6/10) and/or moderate purplish red (5 RP 5/10) in marginal and center field areas of the blades and purplish white (5 RP 9/1), pinkish white (10 RP 9/1) and/or yellowish white (10 Y 9/1) in the basal areas of the blades.
Tube forming series of tepals:
*Number.*—9.
*Size (at full bloom).*—Perianth tube: Length (base to keel) — 26 mm. along tube axis. Major axis — 11 mm. at throat interior. Minor axis — 8 mm. at throat interior. Blades: Maximum length (keel-tip) — 45 mm. Minimum length (keel-tip) — 30 mm. Maximum blade width: 20 mm. Minimum blade width: 16 mm.
*Color.*—Perianth tube: A major field of pinkish white (5 R 9/1) with random striations of purplish white (5 RP 9/1) and/or pale purplish pink (5 RP 9/2).
*Blades.*—Moderate purplish red (5 RP 5/10) in basal areas of blades and dark purplish pink (5 RP 6/8) in marginal and center field areas of the blades.
Androecium:
*Stamen number.*—Tube attached group: 75. Basally united group: 23.
*Filaments.*—Color: Translucent white. Size (at full bloom): Length — Tube attached group: 44 mm. (avg.). Basally united group: 49 mm. (avg.). Diameter: About 0.35 mm. intermediate the opposite ends.
*Anthers.*—Color (before dehiscing): Pale yellow (2.5 Y 9/4) and/or yellowish white (2.5 Y 9/2).
Gynoecium (pistil):
*Style.*—Color: Deep purplish pink (7.5 RP 6/1) and/or moderate purplish pink (5 RP 7/8) in basal area and moderate purplish pink (5 RP 5/10) in distal area. Size (at full bloom): Length — 63 mm. Diameter — 0.85 mm. intermediate the opposite ends.
*Stigma.*—Color: Moderate purplish red (7.5 RP 5/8) (10 RP 5/8) (5 RP 5/10). Size: 3.5 mm. (avg.) lobe length.
*Ovary.*—Color: Strong yellow green (2.5 GY 6/8) and/or moderate yellow green (2.5 GY 5/6) (5 GY 5/6). Size (at full bloom): Length (insertion to concavity base) — 9 mm. Major axis — 9 mm. at distal end of concavity. Minor axis — 2.5 mm. at distal end of concavity.

I claim:

1. The new and distinct plant variety of the Cactaceae family as described and illustrated and which is principally distinguished by a growth habit combining the following characteristics
(1) about the same growth rate, tendency to branch when pruned, and specimen size at comparable stages of maturity as is evident in the 'Lavender Doll' variety,
(2) a greater natural tendency to branch without pruning and a much greater tendency to form more compact specimens with a more upright and erect posture at maturity than the 'Lavender Doll' variety, the phylloclades being usually shorter in length and narrower in width than those of the 'Lavender Doll' variety,
(3) a greater resistance to bud abscission and slightly greater tendency to form multiple buds on the branch tips than the 'Lavender Doll' variety,
(4) a habit of producing more blooms with about the same bloom life and at a noticeably earlier date in the blooming season on specimens of comparable maturity and size when compared with the 'Lavender Doll' variety,
(5) a slightly greater resistance to nutrient deficiencies and to known problem diseases of the related varieties as compared to the 'Lavender Doll' variety,
(6) a bloom which in color closely resembles the bloom of the 'Lavender Doll' variety but which, at full bloom, appears more robust and may be distinguished therefrom by
(a) a sepaloid series of tepals that have a smaller number of tepals, and tepals with shorter length dimensions and narrower blade widths,
(b) a tube laminating series of tepals that have tepals with shorter length dimensions,
(c) a tube forming series of tepals that have tepals with longer length dimensions and slightly greater blade widths, and
(d) a perianth tube which is conspicuously shorter in length,
(7) sterile specimens.

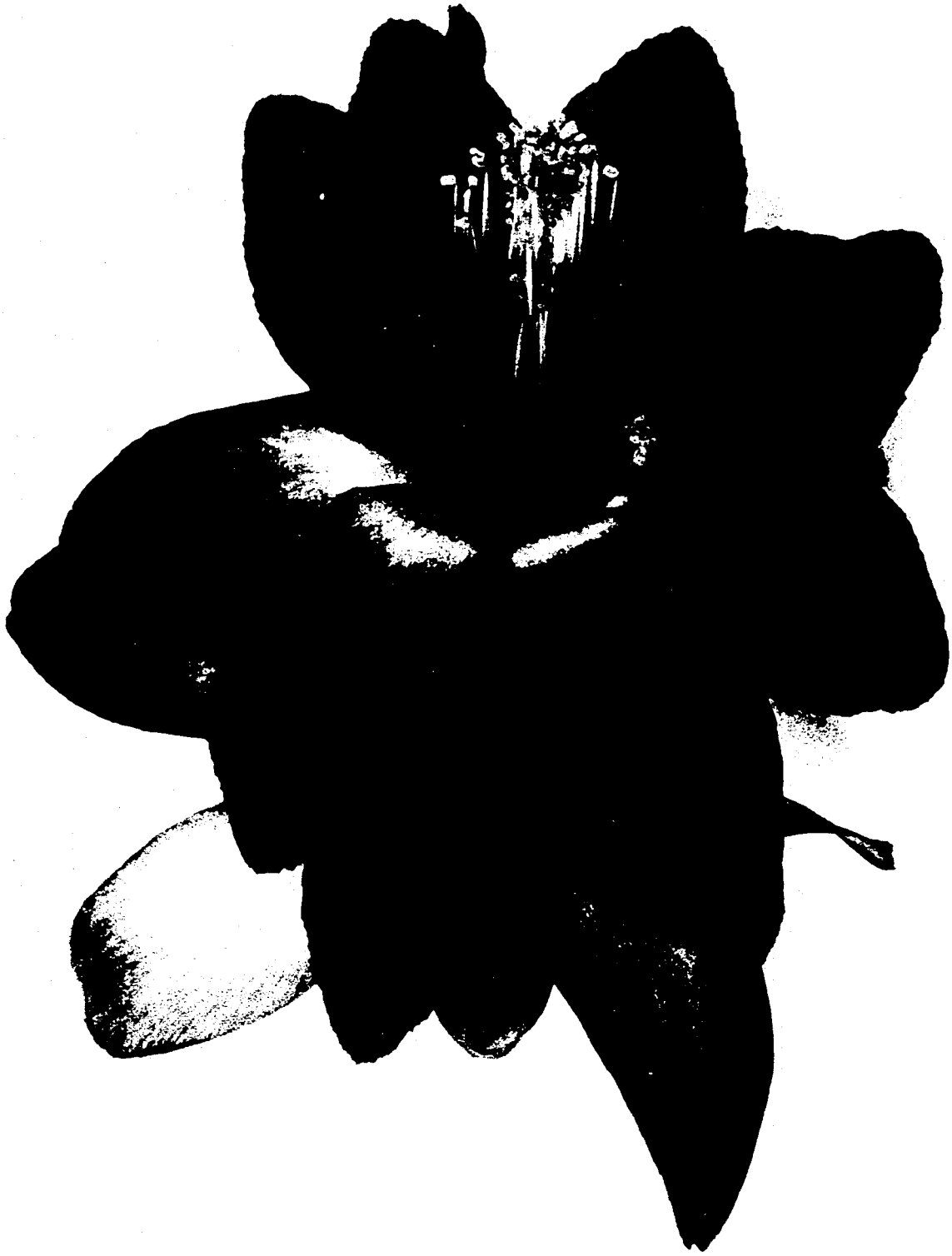

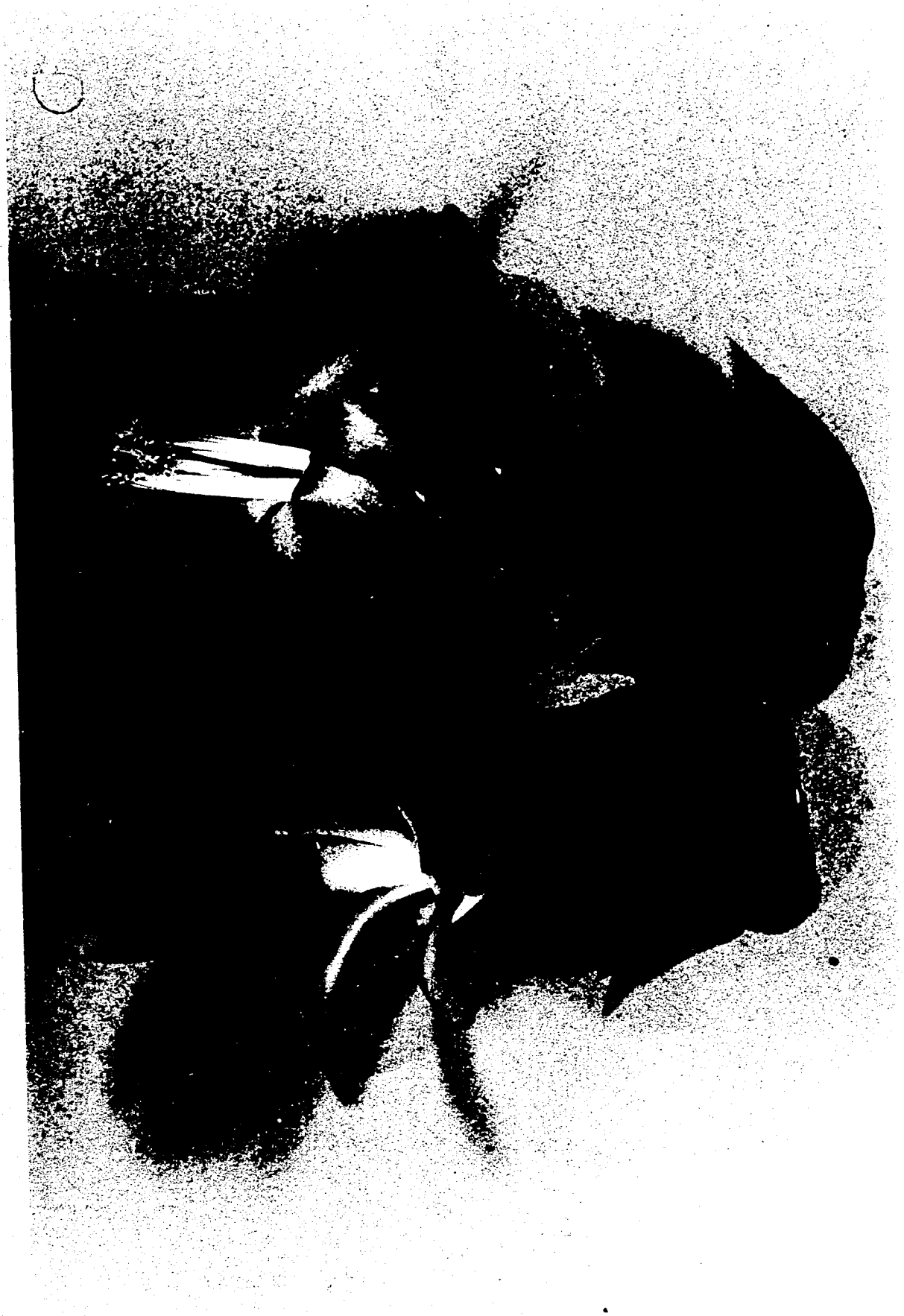

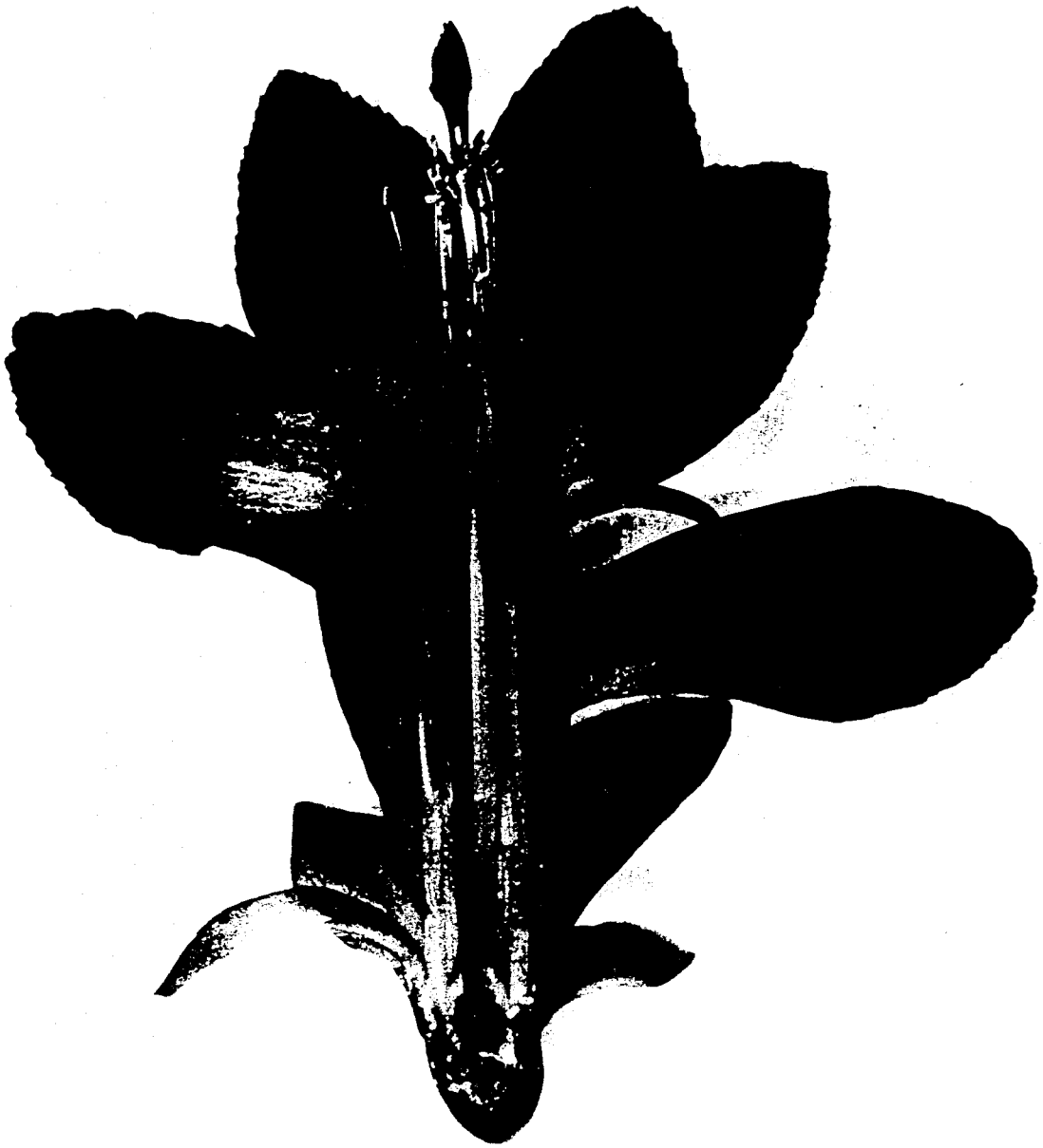

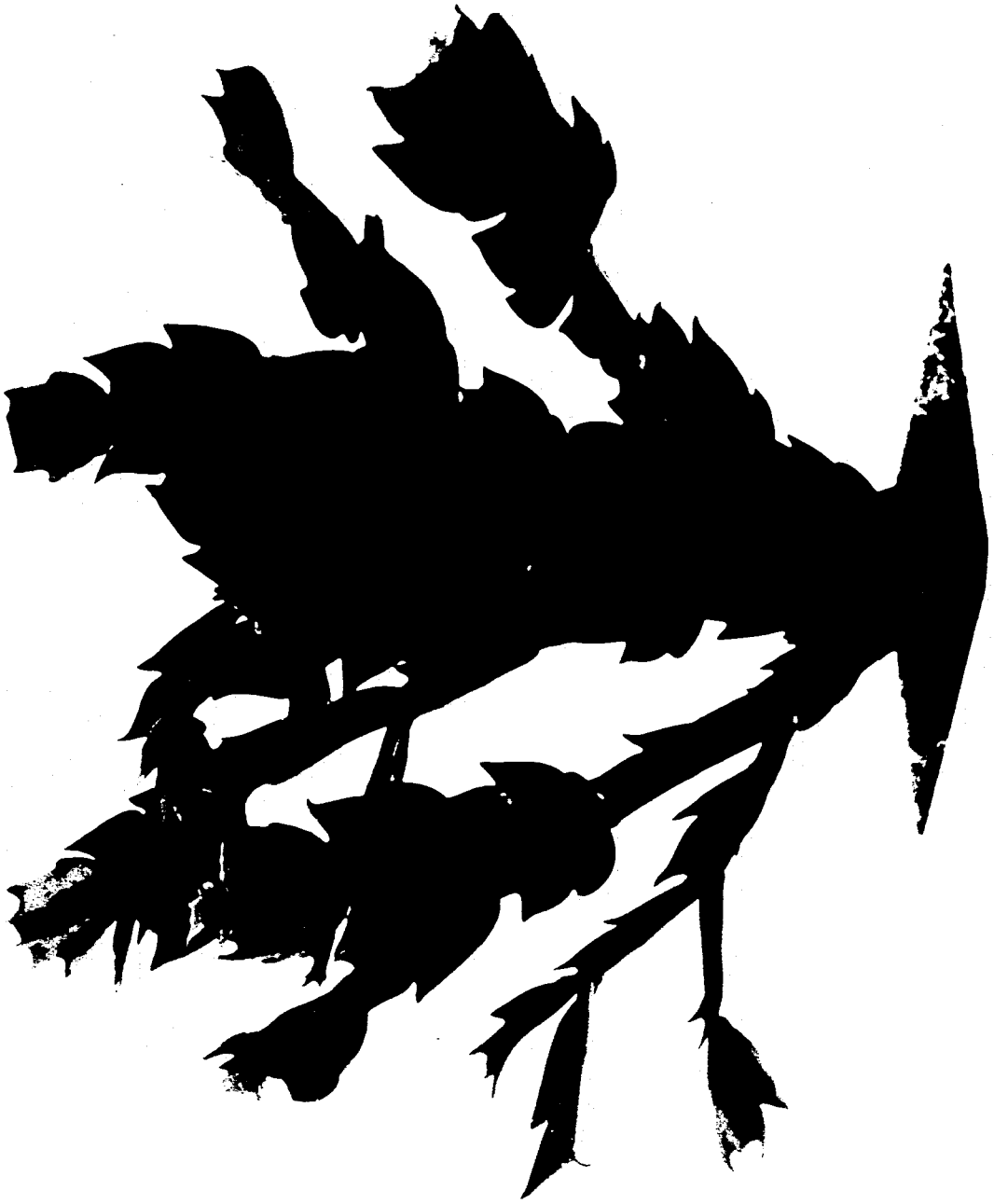

* * * * *